United States Patent
Sim et al.

(10) Patent No.: US 7,932,046 B2
(45) Date of Patent: Apr. 26, 2011

(54) DETECTION METHOD OF BIO MATERIAL, FABRICATION METHOD OF CHIP FOR DETECTION OF BIO MATERIAL, AND CHIP FOR DETECTION OF BIO MATERIAL

(75) Inventors: Sang Jun Sim, Seoul (KR); Jun Pyo Kim, Gyeonggi-do (KR); Cheol Hee Park, Gyeonggi-do (KR)

(73) Assignee: Sungkyunkwan University Foundation for Corporate Collaboration, Gyeonggi-do (KR)

( * ) Notice: Subject to any disclaimer, the term of this patent is extended or adjusted under 35 U.S.C. 154(b) by 32 days.

(21) Appl. No.: 12/317,954

(22) Filed: Dec. 31, 2008

(65) Prior Publication Data

US 2009/0291454 A1 Nov. 26, 2009

(30) Foreign Application Priority Data

May 22, 2008 (KR) ........................ 10-2008-0047683

(51) Int. Cl.
*C12M 1/34* (2006.01)
*G01N 21/00* (2006.01)
*G01N 33/53* (2006.01)
*G01N 33/543* (2006.01)

(52) U.S. Cl. .................. 435/7.1; 435/287.1; 435/287.2; 435/287.9; 435/808; 436/164; 436/518; 436/829; 436/905

(58) Field of Classification Search .................. None
See application file for complete search history.

(56) References Cited

U.S. PATENT DOCUMENTS

| | | | |
|---|---|---|---|
| 6,277,652 B1 * | 8/2001 | Jo et al. ..................... | 436/518 |
| 6,306,598 B1 * | 10/2001 | Charych et al. ................ | 435/6 |
| 6,468,759 B1 * | 10/2002 | Charych ..................... | 435/7.4 |
| 2003/0175812 A1 * | 9/2003 | Reppy et al. ................ | 435/7.1 |

FOREIGN PATENT DOCUMENTS

| | | |
|---|---|---|
| JP | 2007161717 | 6/2007 |
| WO | 2004090165 A1 | 10/2004 |
| WO | 2007016257 A2 | 2/2007 |

OTHER PUBLICATIONS

Jung et al (Small vol. 4, No. 10, pp. 1778-1784, 2008).*
Park et al (Biotechnology Journal vol. 3, No. 5, pp. 687-693, 2008).*
Park et al (Nanotechnology vol. 19, No. 23, pp. 235103/1-235103/7, 2008).*
Park, master's thesis, Chemical Engineering School of Sungkyunkwan University, "Development of label-free sensor system based on arrayed PDS liposme," Feb. 2008.

* cited by examiner

*Primary Examiner* — Mark Navarro
(74) *Attorney, Agent, or Firm* — Kinney & Lange, P.A.

(57) ABSTRACT

Provided are a method for detecting biomaterials, a method for fabricating a chip for biomaterial detection and a chip for biomaterial detection. The method for detecting biomaterials is characterized by comprising the steps of: (S1) immobilizing polydiacetylene liposomes onto a substrate; (S2) linking the polydiacetylene liposomes together and layering them on the substrate; (S3) immobilizing a material which forms a complementary binding with a subject biomaterial to be detected onto the polydiacetylene liposomes; (S4) exposing the resulted polydiacetylene liposome to UV light so as to form a chip for biomaterial detection; (S5) applying the subject biomaterial to be detected to the chip for biomaterial detection for reaction; and (S6) measuring a fluorescent signal from the chip for biomaterial detection.

26 Claims, 19 Drawing Sheets

FIG. 7

*Bar chart showing Signal (y-axis, 0-250) vs Concentration of C. parvum (x-axis: Control, 10², 10³, 10⁴, 10⁵, 10⁶, 10⁷)*

FIG. 12

DETECTION METHOD OF BIO MATERIAL, FABRICATION METHOD OF CHIP FOR DETECTION OF BIO MATERIAL, AND CHIP FOR DETECTION OF BIO MATERIAL

CROSS-REFERENCE TO RELATED APPLICATIONS

This application claims the benefit of Korean Patent Application No. 10-2008-0047683 filed with the Korean Intellectual Property Office on May 22, 2008, the disclosure of which is incorporated herein by reference in its entirety.

BACKGROUND

1. Technical Field

The present invention relates to a method for detecting a biomaterial. Particularly, the present invention relates to a method for detecting a biomaterial, which can detect antigen in rapid and convenient way, from the color transition of a nano-probe made of polydiacetylene (PDA) of which color can be changed by applying stimuli.

2. Description of the Related Art

Most types of polydiacetylene biosensors use a synthetic receptor, while sensors wherein antibodies are selectively immobilized have been hardly found so far. In 2003, an immunodetective method using polydiacetylene was developed and disclosed in a US research. However, its fabrication method is so complicated that a novel immunodetective alternative has still been in need.

Currently, many researches related to polydiacetylene are being made in various parts of the world, but most of those researches are only in the level of experiments on the physical and chemical properties of polydiacetylene molecules, providing theoretical grounds for its potential use as a biosensor. The present inventors believe that the domestic studies on polydiacetylene sensors have already reached to world-class level, and further to the leading position particularly in the technical field of chip fabrication using polydiacetylene.

As for quantitative measures using antibodies, Enzyme Immunoassay (EI), Enzyme-Linked Immunosorbent Assay (ELISA) and Radioimmunoassay (RIA) may be generally mentioned.

The ELISA method which uses an antigen-antibody reaction with an antibody bound with an enzyme is being increasingly used, owing to its advantages such as great sensitivity as much as that of RIA, while using no radioactive ray. However, it also has disadvantages such that it requires a great amount of samples for the assay, a long reaction time and various steps to be taken. As for RIA which shows the highest sensitivity among other methods, it has a risk of using radioactive materials.

For solving the problems of prior arts, other analytical methods which use isotope, fluorescence and enzyme reaction and are capable of exhibiting signal transformation, have been suggested. Among such alternatives, a method using isotope measurement has a safety problem; a method using an enzyme reaction shows a narrow analytical range, thereby not being suitable for samples at various concentrations; and a method using fluorescence measurement needs a step of binding a costly fluorescent material to protein to be detected for use.

In order to dissolve such problems, label-free detection methods such as those using polydiacetylene have been suggested. Polydiacetylene refers to a polymer of diacetylene monomers, having alternate triple bonds. Diacetylene is known to form a supramolecule like a liposome, Langmuir-Blodgett (LB) or Langmuir-Schaeffer (LS) monolayer, owing to its amphoteric property. When diacetylene supramolecule is exposed to UV light, polymerization occurs between adjacent diacetylenes, developing a blue color. The polymerized polydiacetylene supramolecule has a unique property of specific blue-to-red color transition by various stimuli such as temperature, pH change, friction, surfactant, solvent or the like. The color transition of polydiacetylene is determined by the length of n-conjugation in the polymer and the resulting conformation of the molecules. Owing to the characteristics, it is possible to fabricate various types of sensors by varying the conjugation in polydiacetylene polymers. However, such polydiacetylene biosensors in prior arts produce a weak signal on materials to be detected due to instable polydiacetylene immobilization.

In order to solve the technical problems of prior arts, the present invention provides a method for detecting biomaterials which can effectively detect a biomaterial at low concentration by reinforcing the interlinks between polydiacetylene liposomes owing to the use of an interlinker such as diamine, thereby making the polydiacetylene liposomes layered in a sensor chip and thus amplifying the fluorescent signal.

The present inventors have made a great effort to solve the technical problems of conventional arts, and developed a method comprising fabricating a chip by rigidly binding polydiacetylene liposomes and immobilizing the layers thereof onto a substrate, reacting the resulted chip with a biomaterial and confirming an amplified calorimetric signal owing to color transition upon said reaction, thereby completing the present invention.

SUMMARY

The present invention discloses a method for detecting biomaterials characterized by comprising the steps of: (S1) immobilizing polydiacetylene liposomes onto a substrate; (S2) linking the polydiacetylene liposomes together and layering them on the substrate; (S3) immobilizing a material which forms a complementary binding with a subject biomaterial to be detected onto the polydiacetylene liposomes; (S4) exposing the resulted polydiacetylene liposomes to UV light so as to form a chip for biomaterial detection; (S5) applying the subject biomaterial to be detected to the chip for biomaterial detection for reaction; and (S6) measuring a fluorescent signal from the chip for biomaterial detection.

The polydiacetylene liposome can be prepared, for example from a mixture of PCDA (10,12-Pentacosadiynoic-acid) and DMPC (1,2-Dimyristoyl-sn-Glycero-3-phosphocholine). Regarding the production efficiency of liposome and process readiness, the mixing ratio of PCDA and DMPC is preferably in the range of 9:1~6:4, and the temperature at the time of mixing PCDA and DMPC is preferably in the range of 4~100° C.

In the above, it is preferred that PCDA includes one or more functional groups selected from the group consisting of sulfone, amine and carboxyl.

In the step (S2), the polydiacetylene liposomes can be interlinked together by using an interlinker. The interlinker comprises the same or different two or more functional groups being capable of binding with the functional groups of the liposome, for example sulfone, amine or carboxyl group. Illustrative of such interlinkers are diamine, dithiol, dicarboxylic acid, diol, streptavidin and the like. The interlinker is preferably present at the concentration of more than 0 mM and not more than 20 mM. When the concentration is more than 20 mM, it would undesirably occur that the surface of liposome in excessive range could be substituted by amine groups.

The step (S1) can be achieved by substituting the substrate and polydiacetylene liposomes with for example, amine and carboxyl groups, respectively, and then using a NHS(N-Hydroxysuccinimide)/EDC (1-ethyl-3-[3-dimethylamino-propyl]carbodiimide hydrochloride) reaction between amine and carboxyl groups. In the above, EDC helps carboxyl groups to be activated and bound with amine groups so as to form amide bonds. At this time, for increasing the binding efficiency, NHS is added to the reaction. Since the NHS/EDC reaction is well known in this field of art, we believe that specific descriptions on this matter dose not needed to be further illustrated in this specification.

However, the NHS/EDC reaction is preferably carried out at a temperature in the range of 0~37° C. The step (S1) may also be carried out by substituting the substrate and the polydiacetylene liposomes with inter-reactive functional groups other than amine and carboxyl group and allowing them to react. For example, for PCDA-MI that is PCDA bonded to maleimide, a substrate substituted with thiol groups (—SH) can be used to immobilize polydiacetylene liposomes onto the substrate.

The immobilization of an antibody in the step (S4) can be achieved by using NHS/EDC reaction.

In the step (S4), the polydiacetylene liposome is preferably exposed to UV light for 10 seconds to 10 minutes. When the exposure is less than 10 seconds, the color formation in liposomes to blue is limitatively conducted, and when it is more than 10 minutes, it gives too much stress to the liposomes which already has got a blue color, causing further color change to red.

In the step (S5), the application of a subject biomaterial to be detected to the biomaterial detection chip for reaction, is preferably carried out at a temperature in the range of 0~50° C. When the reaction temperature is out of said range, the subject biomaterials could be damaged.

The method for detecting biomaterials of the present invention can be widely utilized for the detection of materials which form complementary bindings or perform immune reactions, such as antigen-antibody, enzyme-substrate and the like.

The biomaterials may be at least one selected from the group consisting of pathogens, DNA, RNA, PNA (Peptide Nucleic Acids), oligonucleotides, peptides, proteins, biological membranes, polysaccharides, antigens, antibodies, and cells. Illustrative pathogens may include *Cryptosporidium parvum, Giardia lamblia, E. coli, Salmonella typhimurium, Shigella flexneri*, and *Encephalitozoon intestinalis*, without being limited to these examples.

The method for detecting biomaterials according to the present invention is applicable to all of the biological bindings as well as chemical bindings which may be present in living organisms. Further, the method for detecting biomaterials of the present invention can even sense a very small amount of biomaterials, for example being capable of detecting about $10^2$ unit/ml of pathogen such as *C. parvum*.

The present invention also provides a method for fabricating a chip for biomaterial detection, which comprises the steps of: (S1) immobilizing polydiacetylene liposomes onto a substrate; (S2) linking the polydiacetylene liposomes together and layering them on the substrate; (S3) immobilizing a material which forms a complementary binding with a subject biomaterial to be detected onto the polydiacetylene liposomes; and (S4) exposing the polydiacetylene liposomes to UV light.

The polydiacetylene liposomes can be prepared from a mixture of PCDA and DMPC. Herein, PCDA may comprise one or more functional groups selected from the group consisting of sulfone, amine and carboxyl group.

In the step (S2), the polydiacetylene liposomes can be interlinked by an interlinker. The interlinker comprises the same or different two or more functional groups being capable of binding with the functional groups of the liposome, for example sulfone, amine or carboxyl group. Illustrative of such interlinkers are diamine, dithiol, dicarboxylic acid, diol, streptavidin and the like.

The present invention further provides a chip for biomaterial detection characterized by comprising multilayered polydiacetylene liposomes immobilized on a substrate, wherein the polydiacetylene liposomes have immobilized materials thereon which form a complementary binding with a subject biomaterial to be detected, and develop a blue color by UV light irradiation.

The polydiacetylene liposomes can be prepared from a mixture of PCDA and DMPC. Herein, PCDA may comprise one or more functional groups selected from the group consisting of sulfone, amine and carboxyl group.

The polydiacetylene liposomes can be interlinked together by an interlinker. The interlinker comprises the same or different two or more functional groups being capable of binding with the functional groups of the liposome, for example sulfone, amine or carboxyl group. Illustrative of such interlinkers are diamine, dithiol, dicarboxylic acid, diol, streptavidin and the like, without being limited by these examples.

BRIEF DESCRIPTION OF THE DRAWINGS

The patent or application file contains at least one drawings executed in color. Copies of this patent or patent application publication with color drawings will be provided by the Office upon request and payment of the necessary fee.

FIG. 7 is a graph showing changes in detected signals upon *C. parvum* concentration.

FIG. 12 is a graph showing changes in detected signals upon *Shigella flexneri* concentration as well as the exponential relation between the detected signal value and *Shigella flexneri* concentration.

DETAILED DESCRIPTION

Hereinafter, the present invention is further described in detail.

According to the present invention, it is possible to detect biomaterials in efficient way, owing to significantly amplified chromatic change from an antigen-antibody immune reaction, by using an interlinker such as ethylenediamine in fabrication of a polydiacetylene liposome chip for biomaterial detection for strengthening the linkages among liposomes and thus allowing the liposomes to be layered on the substrate.

Since diacetylenes form an interface with an aqueous solution owing to its amphoteric property, self-assembly can be induced as a form of supramolecule such as a liposome, micelle Langmuir Blodgett or Langmuir Schaeffer film. In forming such supramolecule, if the distance between the diacetylene monomers is sufficiently narrow, they can undergo a polymerization reaction under UV light, developing a blue color due to the newly formed bindings in the polymer. The color of the bindings in the polymer is closely related with π-conjugation participated in the polymerization binding. When stimuli are applied, rearrangement of the monomers in the polymer molecule occurs, and it reduces the length of n-conjugation, developing a gradual color transition of blue to red, depending on the degree of stimuli. The stimuli which can induce such color transition, may generally include temperature, pH, surface abrasion, organic solvents or an interaction with a surfactant. In other methods, by chemical modification of monomers in supramolecule, when the receptors are stood out to the interface, it can be used as a biosensor or biochemical analysis technique, wherein a color transition is induced from a reaction between the receptors and ligands.

Figure 1:
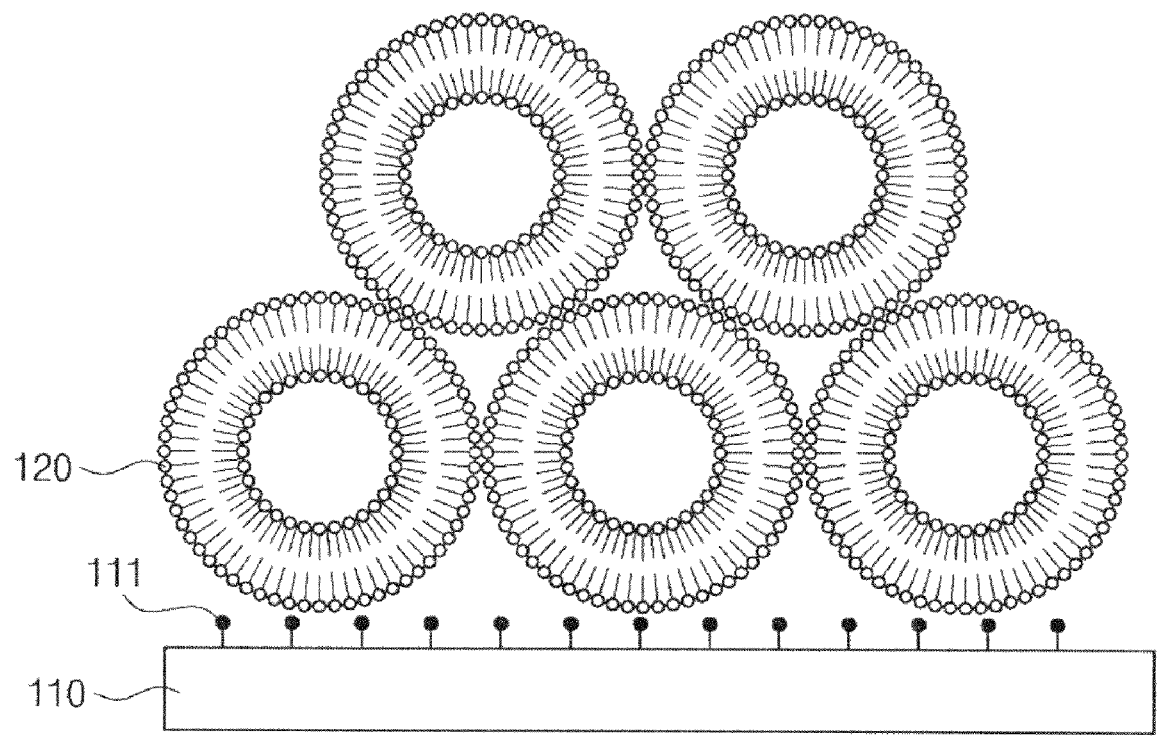
FIGS. 1 to 3 are views schematically illustrating the fabrication process of a chip for biomaterial detection according to the present invention.
Figure 2:
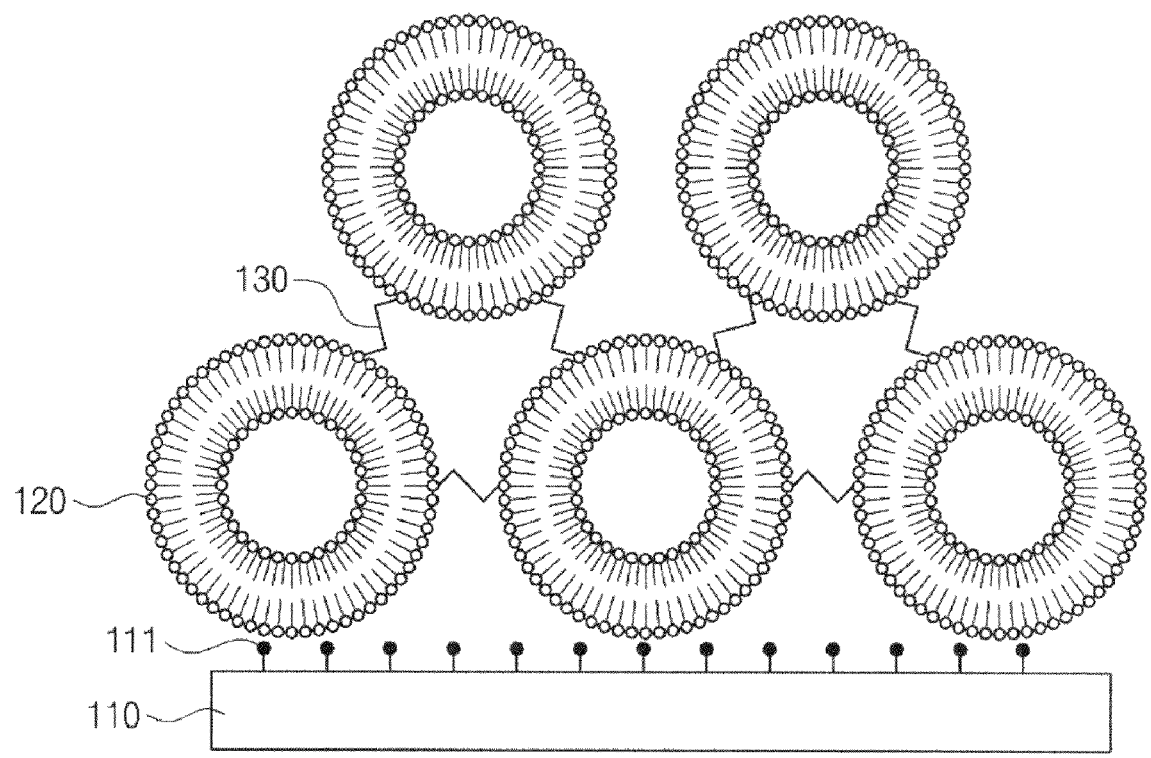
Figure 3:
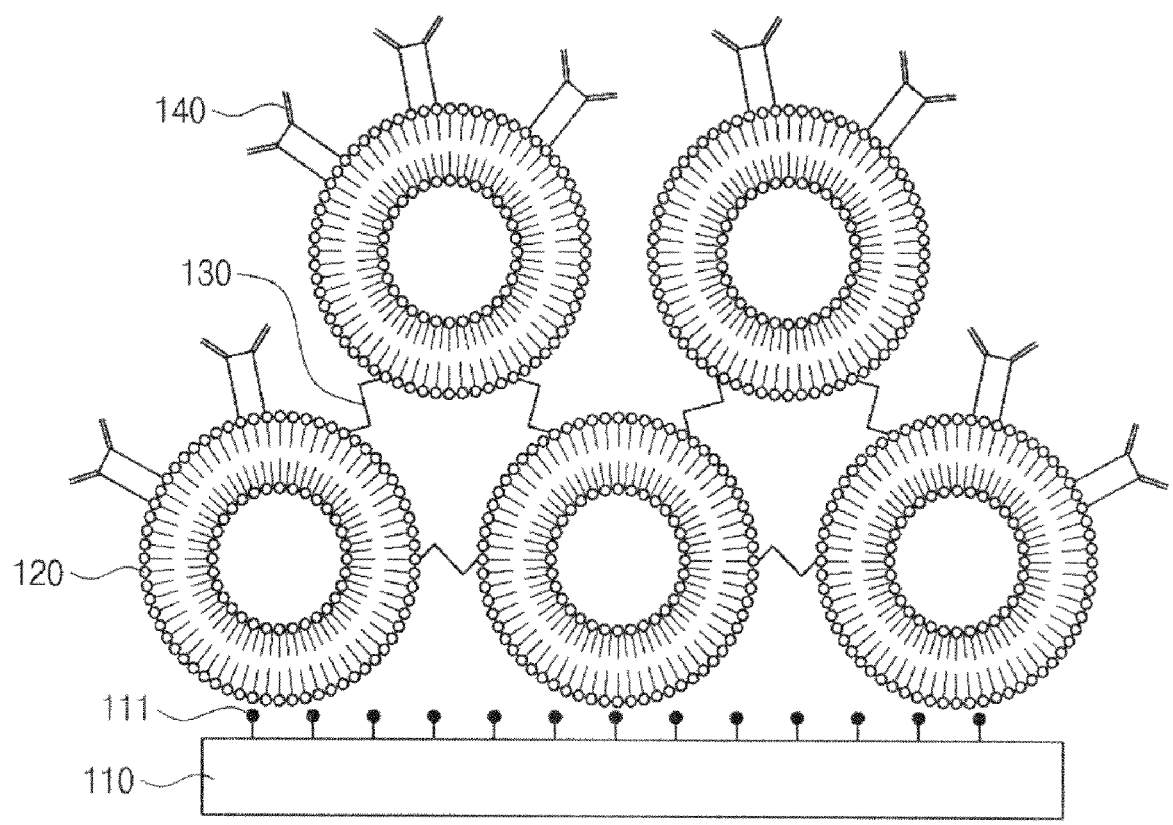

FIGS. 1 to 3 are views schematically illustrating a fabrication process of a chip for biomaterial detection according to the present invention. With a reference to FIGS. 1 to 3, firstly, polydiacetylene liposomes (120) are immobilized onto a substrate (110) (FIG. 1). The amine groups (111) substituted on the substrate react with the carboxyl groups of the polydiacetylene liposomes (120), thereby immobilizing the polydiacetylene liposomes (120). Next, the polydiacetylene liposomes (120) are interlinked together by interlinkers (130) so as to form polydiacetylene liposome layers on the substrate (110) (FIG. 2). Before said step, bindings among the polydiacetylene liposomes (120) are so weak that the polydiacetylene liposomes (120) are easily washed out, thereby being incapable of forming multiple layers. However, as undergone the above-described step, the bindings become stronger, and accordingly it is possible to form a multilayered structure. Then, a material (140) which forms a complementary binding with a biomaterial is immobilized onto the polydiacetylene liposomes (120) (FIG. 3). Finally, the resulted polydiacetylene liposomes are exposed to UV light. Through this irradiation step, the polydiacetylene liposomes develop a blue color.

Hereinafter, the present invention is further illustrated and can be understood by way of examples provided below. However, these examples are only to help understanding of the present invention, by no means limiting the scope of the present invention.

Example

Detection of Pathogens Using a Sensor Chip Comprising Multilayered Polydiacetylene Liposomes 1) Preparation of Polydiacetylene Liposome by Using PCDA and DMPC The present step of liposome preparation and its immobilization onto a glass substrate was carried out by mixing PCDA and DMPC and NHS/EDC reaction. Each of PCDA and DMPC was dissolved in chloroform to a certain concentration (10 mM) and kept in a vial being tightly sealed at −20° C. The resulted two solutions were mixed at a certain molar ratio so as to obtain a final lipid concentration of 1 mM. After mixing PCDA and DMPC at a molar ratio of 8:2, chloroform was evaporated by using a nitrogen gas and a film of lipid was formed on the bottom of the vial. To the lipid film, PBS buffer was added and it was heated at 80° C. for 15 minutes so that the lipid film could be re-dispersed into the buffer. The re-dispersed solution was subjected to an extruder system several times passing through a membrane having penetration pores of 100 nm. During the process, the extruder system was maintained at a temperature of 75° C. so that PCDA lipid structure could be easily formed. The solution which finally passed through the membrane was comprised of a liposome comprising PCDA and DMPC at a dimension of 100 nm. The resulted liposome solution was cooled at room temperature (25° C.) for 20 minutes, being ready to be immobilized to a glass substrate that was substituted with amines.

2) Immobilization and Layering of Polydiacetylene Liposomes

Polydiacetylene liposomes were immobilized onto a glass substrate substituted with amine groups, by using a chemical method. Each of NHS and EDC was dissolved into a PBS buffer (10 mM, pH 7.4) to the concentration of 200 mM. Then, the prepared polydiacetylene liposome solution was mixed with the same amount of NHS/EDC solution and ethylenediamine. At this point, for determining the optimal concentration of ethylenediamine, the test was conducted while varying the concentration of ethylenediamine from 0 mM to 20 mM. The range of ethylenediamine concentration was drawn from consideration that when the ethylenediamine concentration is too high, the outer surface of polydiacetylene liposome would be substituted all over with amines, preventing its immobilization onto the glass substrate, and when the concentration is too low, signal amplification is not effectively achieved. The mixed liposome solution was spotted to a glass substrate substituted with amine by using a microarrayer. The glass substrate having spotted polydiacetylene liposome was stood 2 hours for reaction in a moist container at low temperature (4° C.) for preventing the liposome solution from being evaporated. After completing the reaction, the polydiacetylene liposome substrate was rapidly washed with distilled water and 0.1% Tween-20 solution and then lightly dried by using a nitrogen gas.

3) Immobilization of Antibodies to Pathogens onto Polyacetylene Liposomes

Antibody immobilization was performed by using a NHS/EDC reaction. Antibodies were mixed into 200 mM NHS/EDC solution which was dissolved in PBS buffer, and the resulted mixture was brought to contact for 3 hours with the substrate onto which polydiacetylene liposomes were immobilized. This process was also performed in a moist container at low temperature (4° C.) in order to prevent evaporation of the antibody solution. Completing the contact reaction, it was washed and dried as in the previous step, thereby achieving fabrication of a polydiacetylene liposome sensor chip.

4) Detection of Pathogens: *Cryptosporidium parvum, Giardia lamblia, E. coli* O-157, *Salmonella typhimurium, Shigella flexneri*, and *Encephalitozoon intestinalis*

The above-fabricated sensor chip was exposed to UV light at 254 nm for about 5 minutes. The polydiacetylene liposome sensor chip exposed to UV light developed a blue color, and pathogens (*Cryptosporidium parvum, Giardia lamblia, E. coli* O-157, *Salmonella typhimurium, Shigella flexneri*, and *Encephalitozoon intestinalis*; $10^7$ unit/ml) were applied thereto at 37° C. that was the optimal temperature for an immune reaction. By stress owing to the immune reaction, the color of the polydiacetylene liposome sensor chip was again changed from blue to red. The degree of color transition was estimated by an optical microscope.

Figure 4:
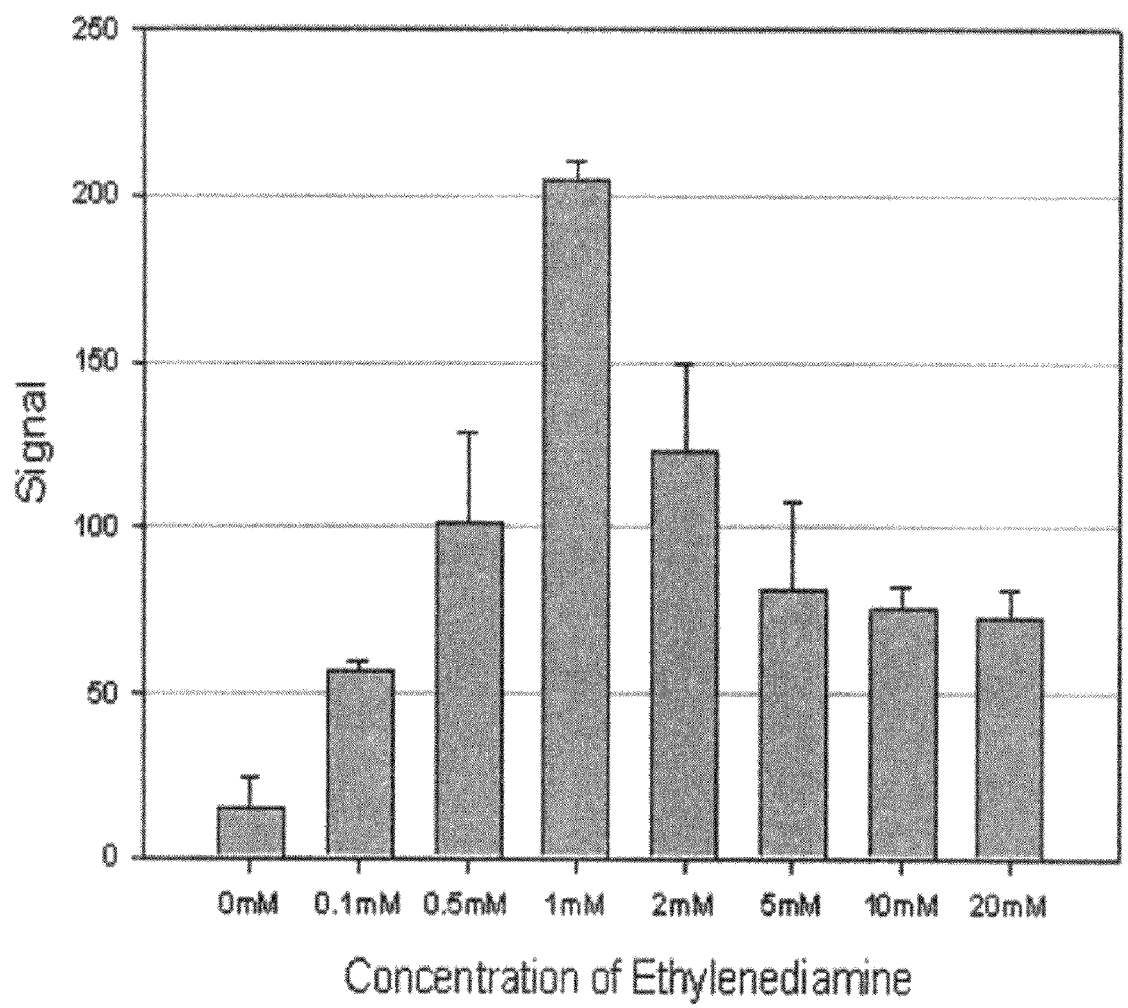
FIG. 4 is a graph representing the signals detecting *C. parvum* according to the interlinker concentration.
Figure 5:
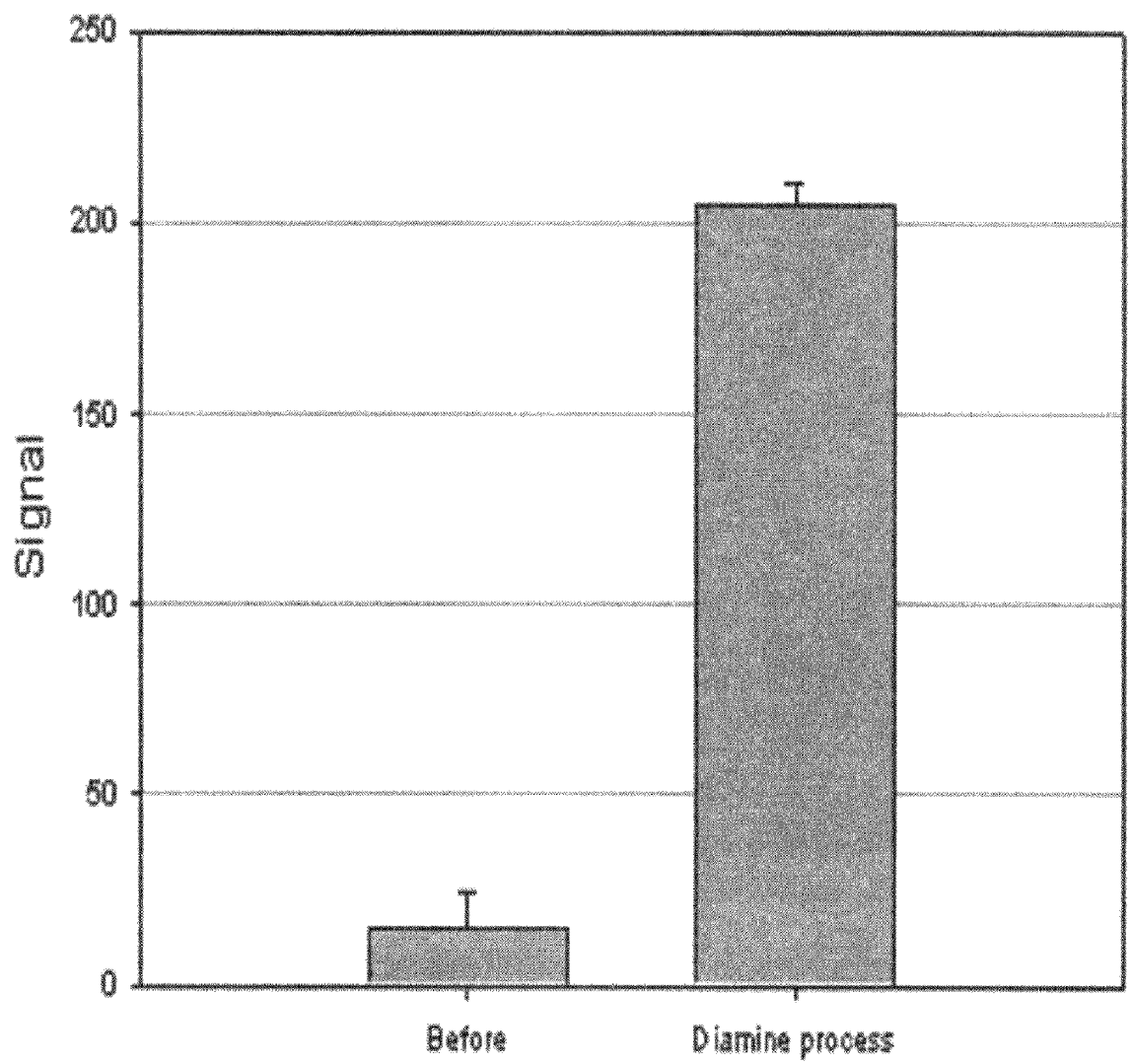
FIG. 5 is a graph comparing signals from two cases, each using: a monolayer of polydiacetylene liposomes immobilized on a substrate without using an interlinker, and multiple layers of polydiacetylene liposomes immobilized by using an interlinker.
Figure 6:
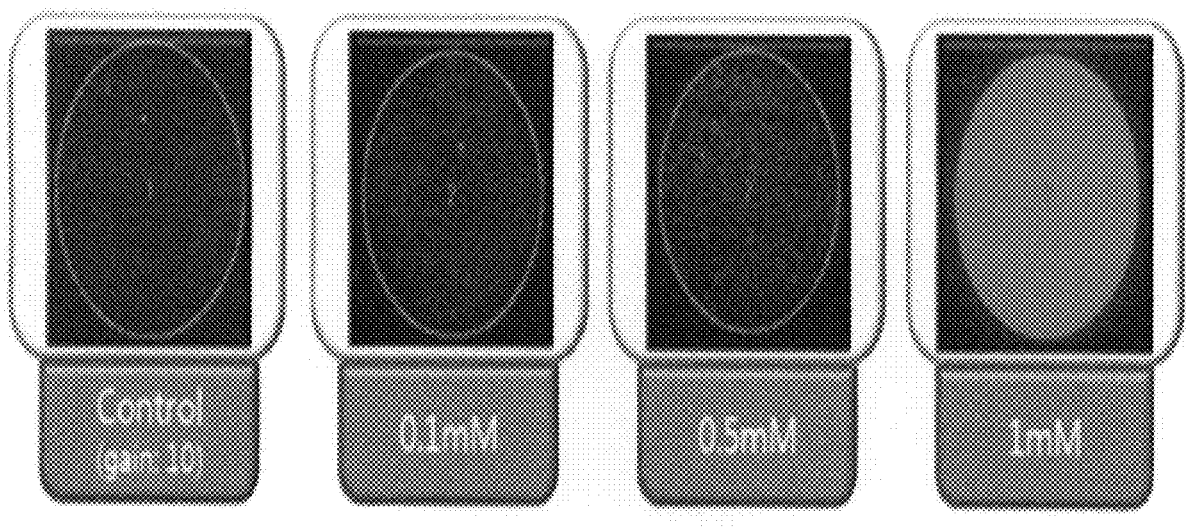
FIG. 6 is images showing color transition according to the detection of *C. parvum* upon various interlinker concentrations.
Figure 6:
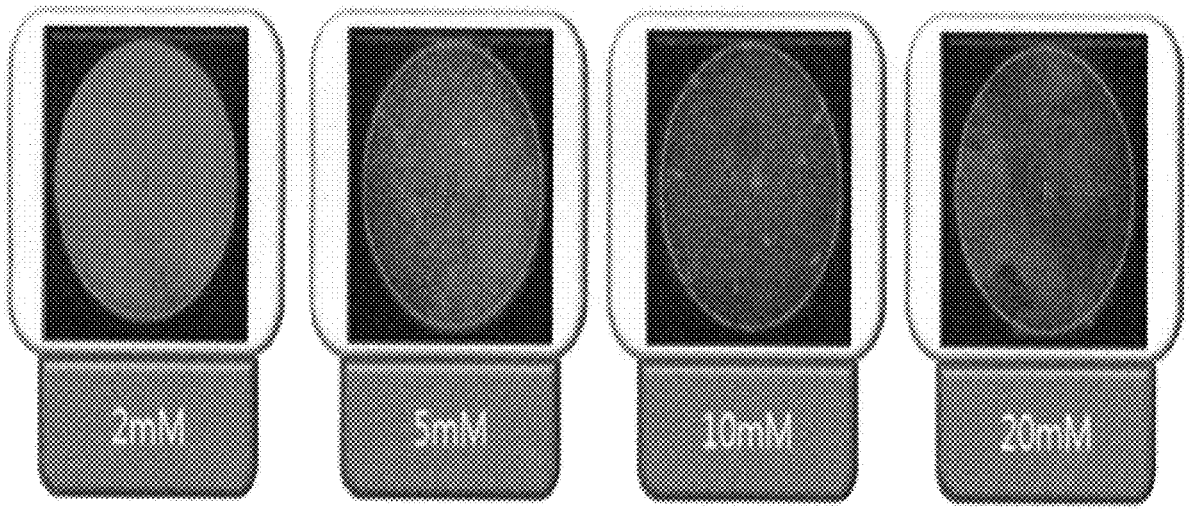

FIGS. 4 to 6 were obtained from the results of the present example: FIG. 4 is a graph representing the detecting signals of *C. parvum* according to the interlinker concentration; FIG. 5 is a graph comparing signals from two cases, each using: a monolayer of polydiacetylene liposomes immobilized on a substrate without using an interlinker, and multiple layers of polydiacetylene liposomes immobilized by using an interlinker; and FIG. 6 is images showing color transition according to the detection of *C. parvum* upon various interlinker concentrations.

By reviewing the analysis results of FIGS. 4 to 6, it was confirmed that the signal was increased along the increase in diamine concentration within the range of 0 mM to 1 mM, however when the concentration is over 1 mM, the signal was decreased along the increase in concentration. The peak signal was about 205 at the time when the diamine concentration was 1 mM, which can be clearly seen from the image. With referencing the graph showing the cases using a conventional method (0 mM diamine) and 1 mM diamine, it could also be found out that the signal was amplified as much as about 20 times.

5) Changes in Signal Detection Upon the Various Pathogen Concentrations

It was found out that, when applying diamine treatment as described above, signals could be significantly amplified as compared to the conventional methods. However, for verifying that such method be suitably applied for functioning as a sensor chip, it is necessary to show that precise and correct signals can be detected according to the concentration of a subject biomaterial. Practically, for detecting pathogenic microorganisms in river water, it was necessary to lower the minimum detection limit since the conventional minimum detection limit was not low enough for practical use. Therefore, in order to verify that it can function well as a sensor chip, a test for detecting pathogens at various concentrations was carried out.

Figure 8:
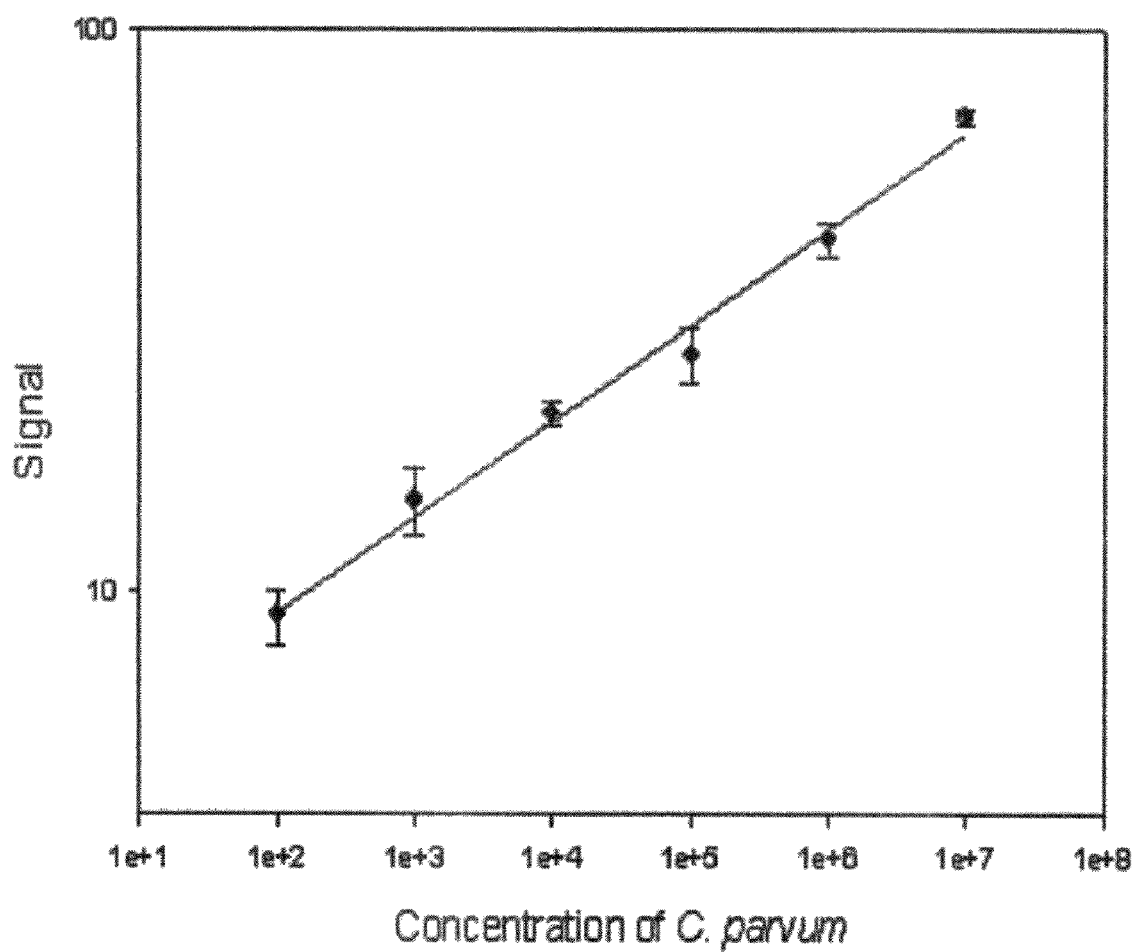
FIG. 8 is a graph showing the exponential relation between the detected signal value and *C. parvum* concentration.
Figure 9:
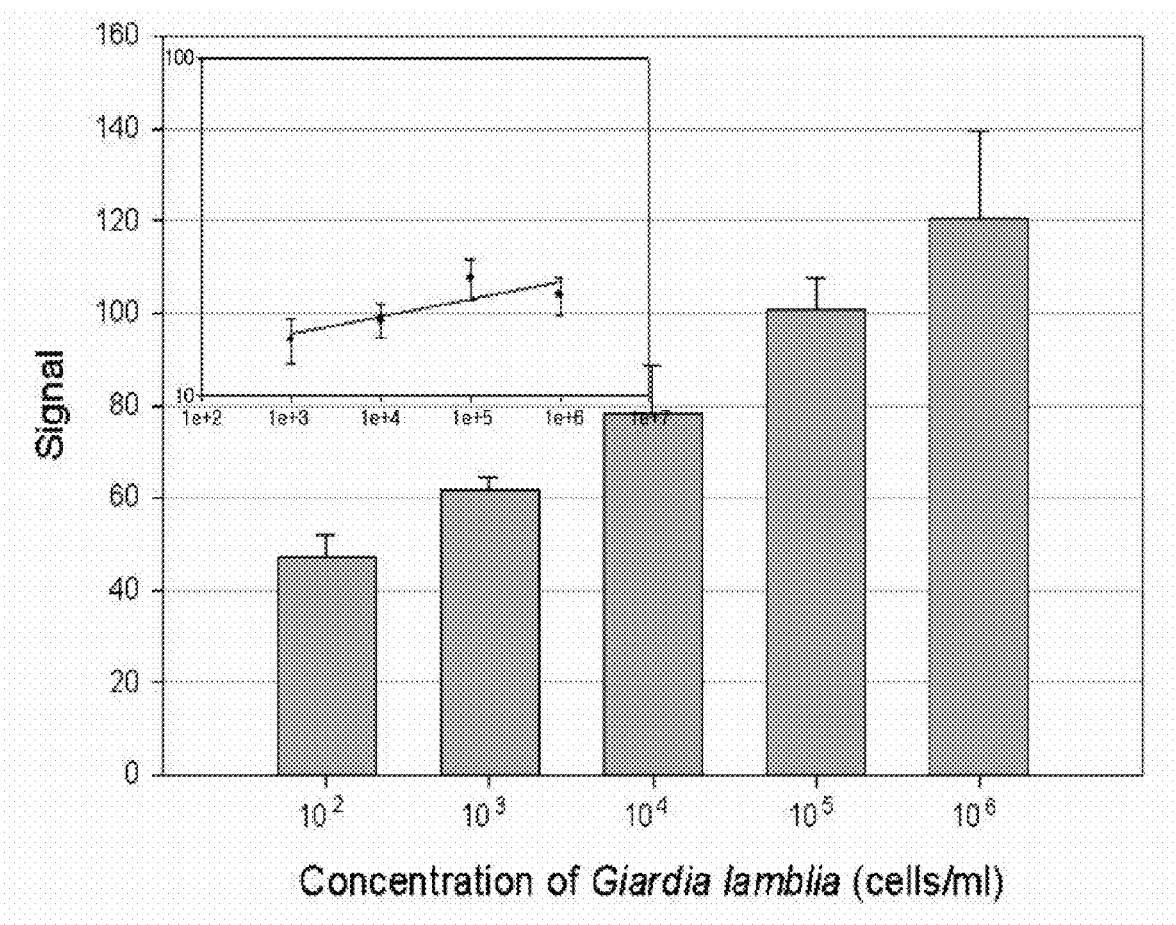
FIG. 9 is a graph showing changes in detected signals upon *Giardia lamblia* concentration as well as the exponential relation between the detected signal value and *Giardia lamblia* concentration.
Figure 10:
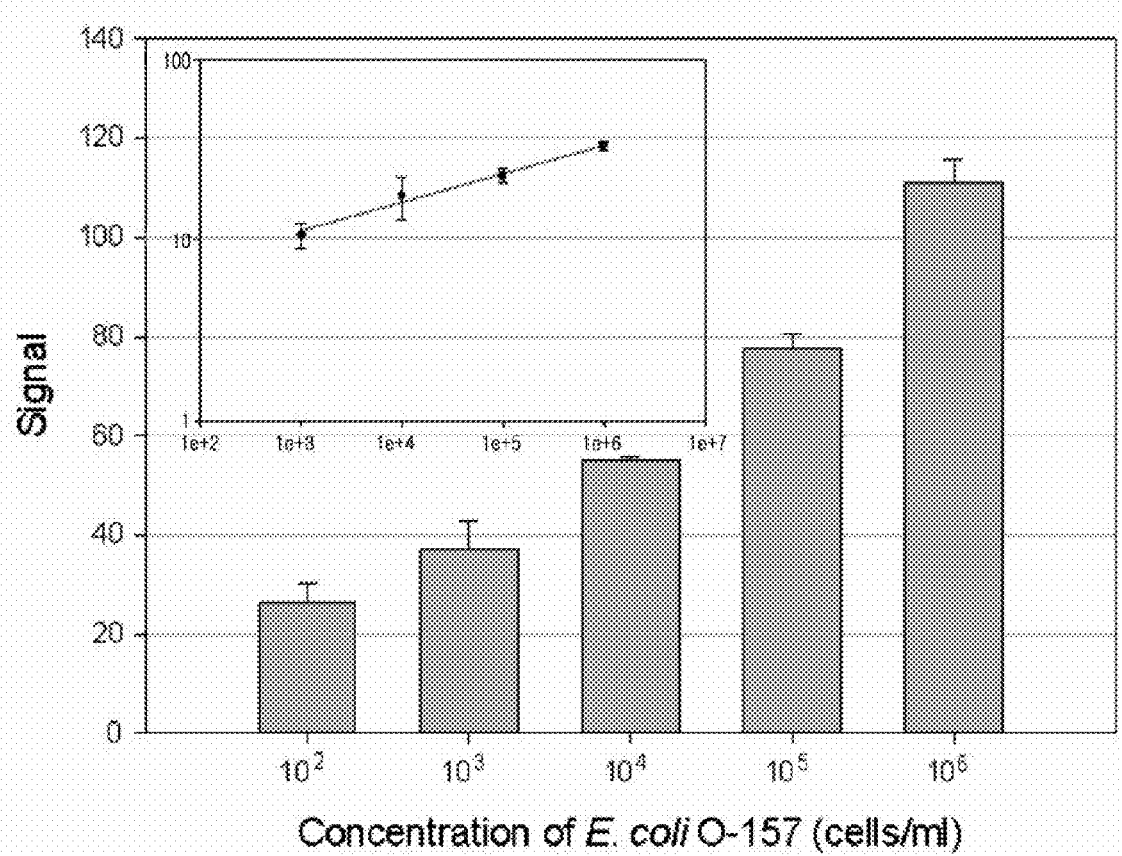
FIG. 10 is a graph showing changes in detected signals upon *E. coli* O-157 concentration as well as the exponential relation between the detected signal value and *E. coli* O-157 concentration.
Figure 11:
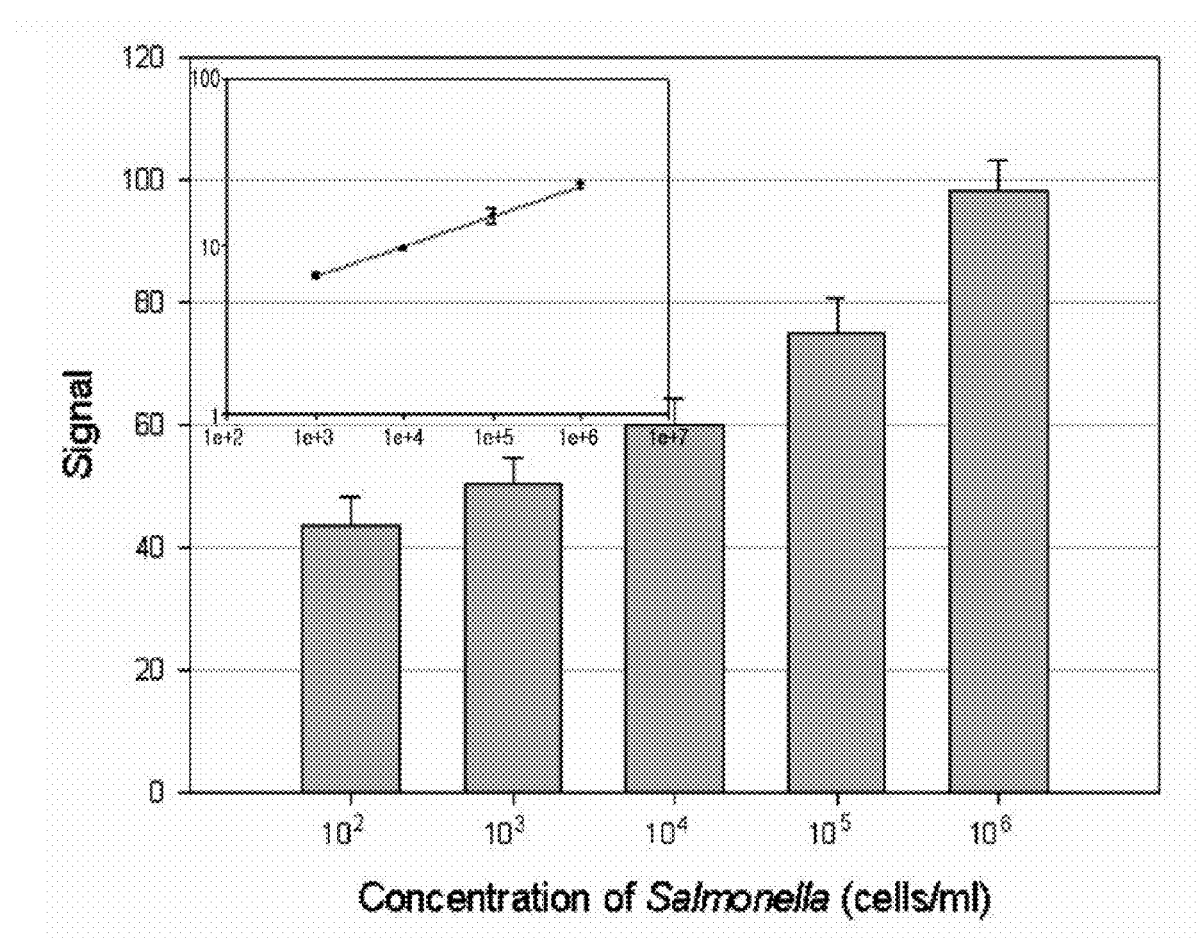
FIG. 11 is a graph showing changes in detected signals upon *Salmonella typhimurium* concentration as well as the exponential relation between the detected signal value and *Salmonella typhimurium* concentration.
Figure 12:
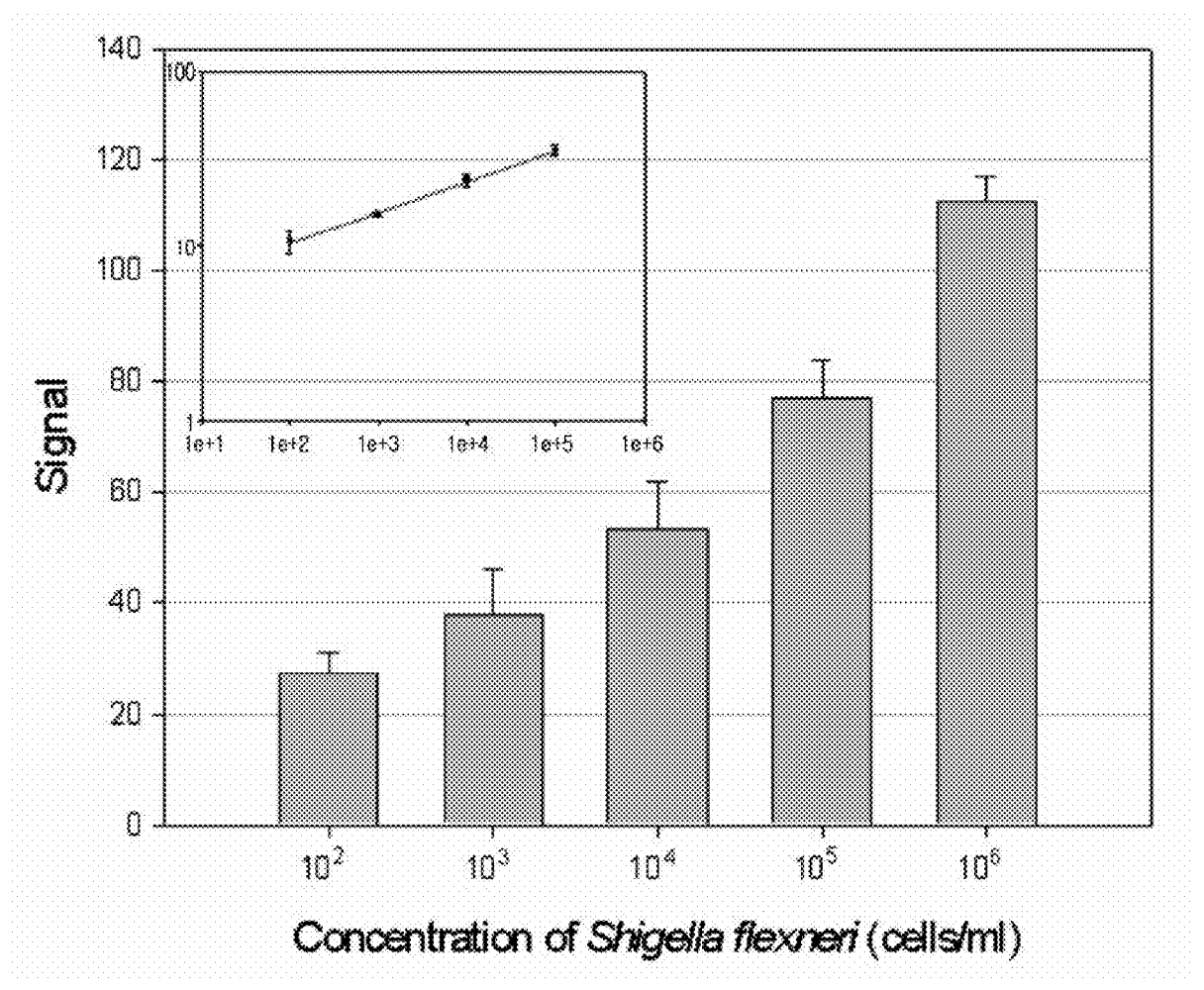
Figure 13:
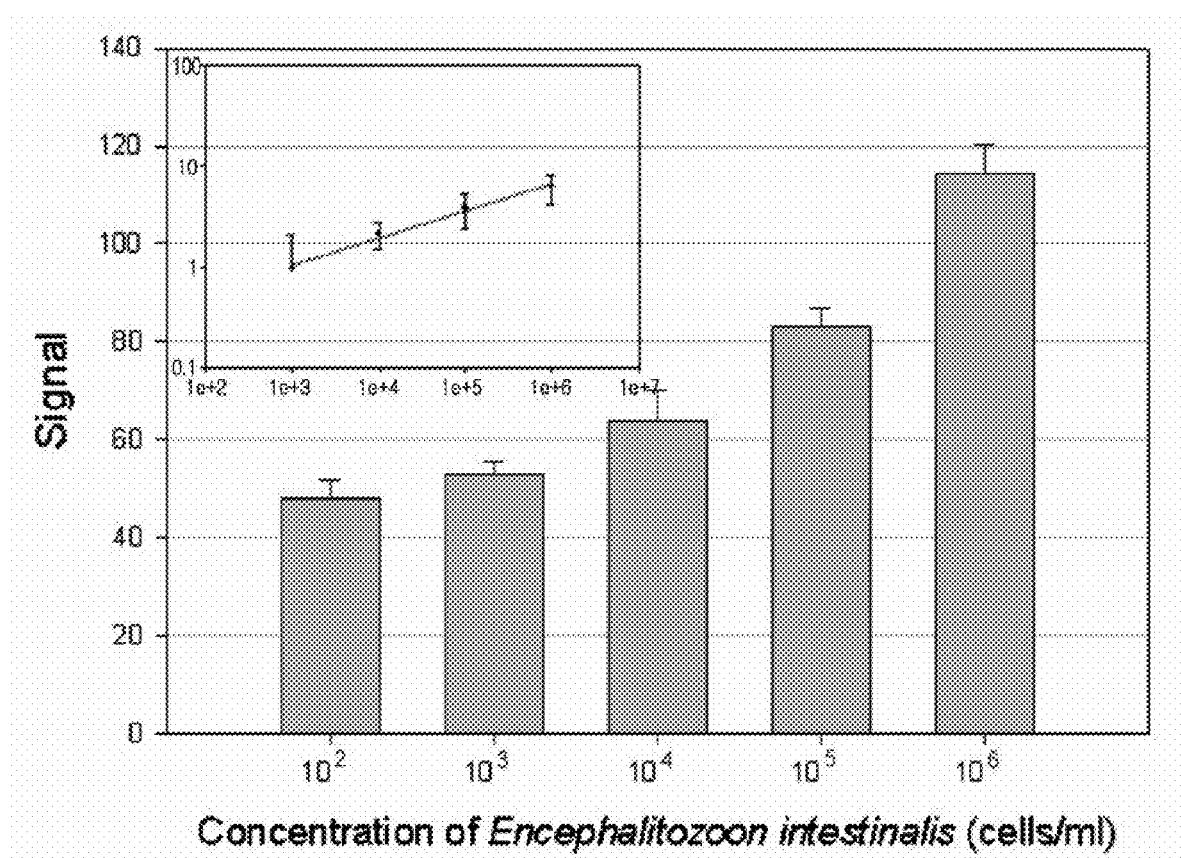
FIG. 13 is a graph showing changes in detected signals upon *Encephalitozoon intestinalis* concentration as well as the exponential relation between the detected signal value and *Encephalitozoon intestinalis* concentration.
Figure 14:
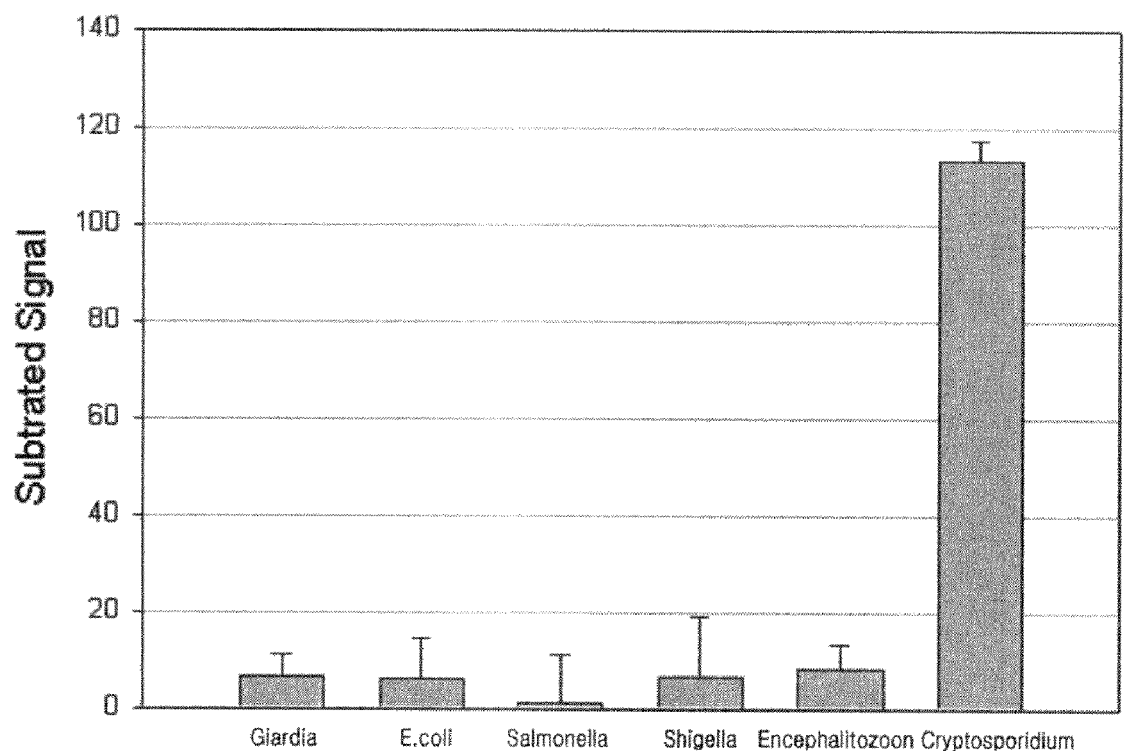
FIGS. 14 to 19 are graphs showing that the fabricated chip for biomaterial detection specifically responds to a desired material to be detected.
Figure 15:
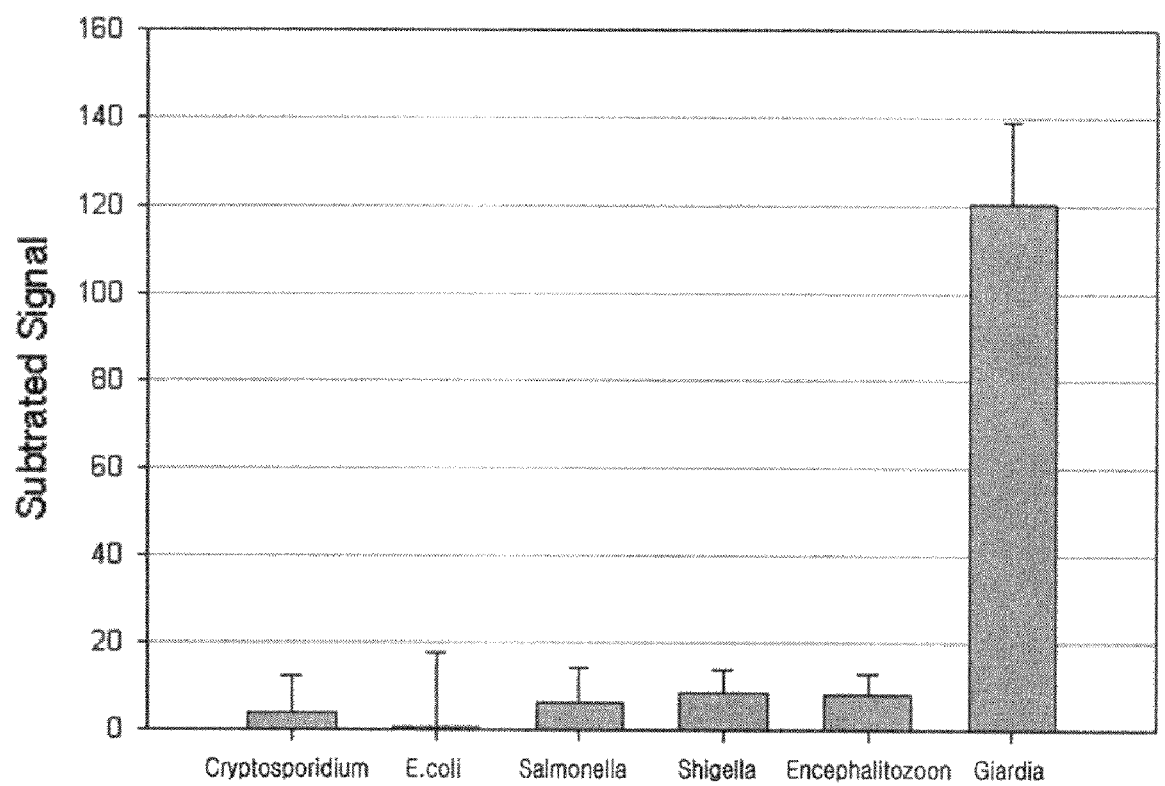
Figure 16:
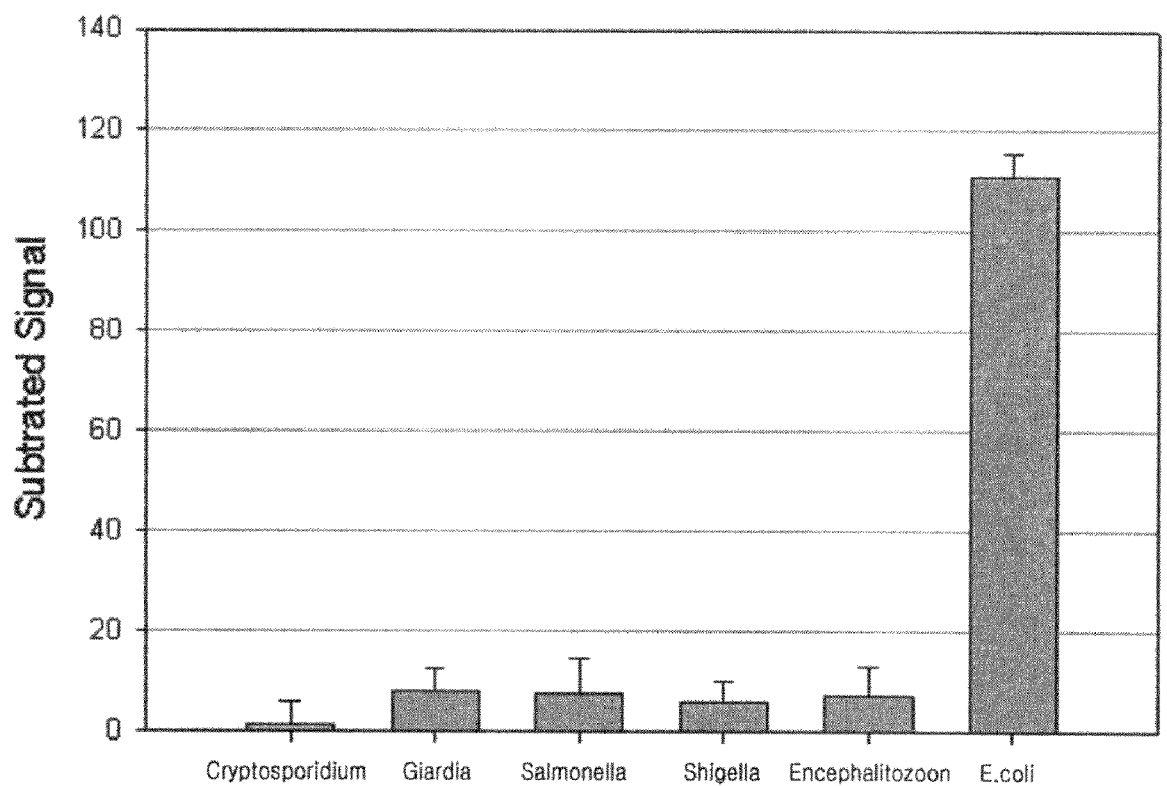
Figure 17:
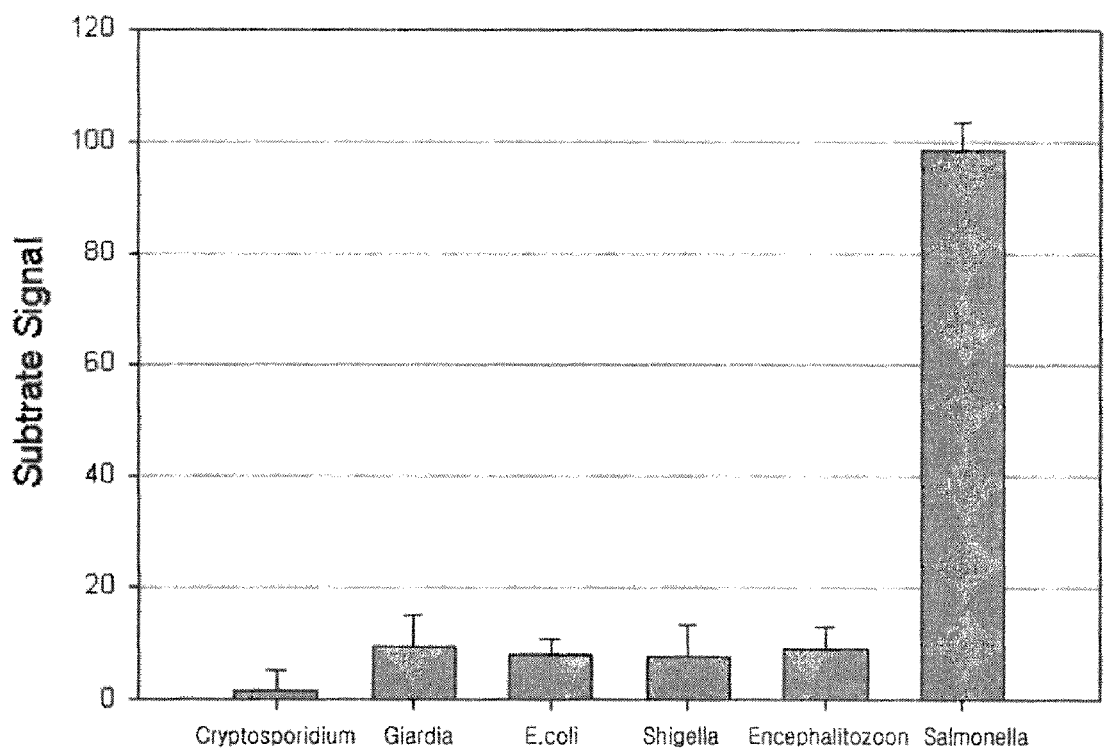
Figure 18:
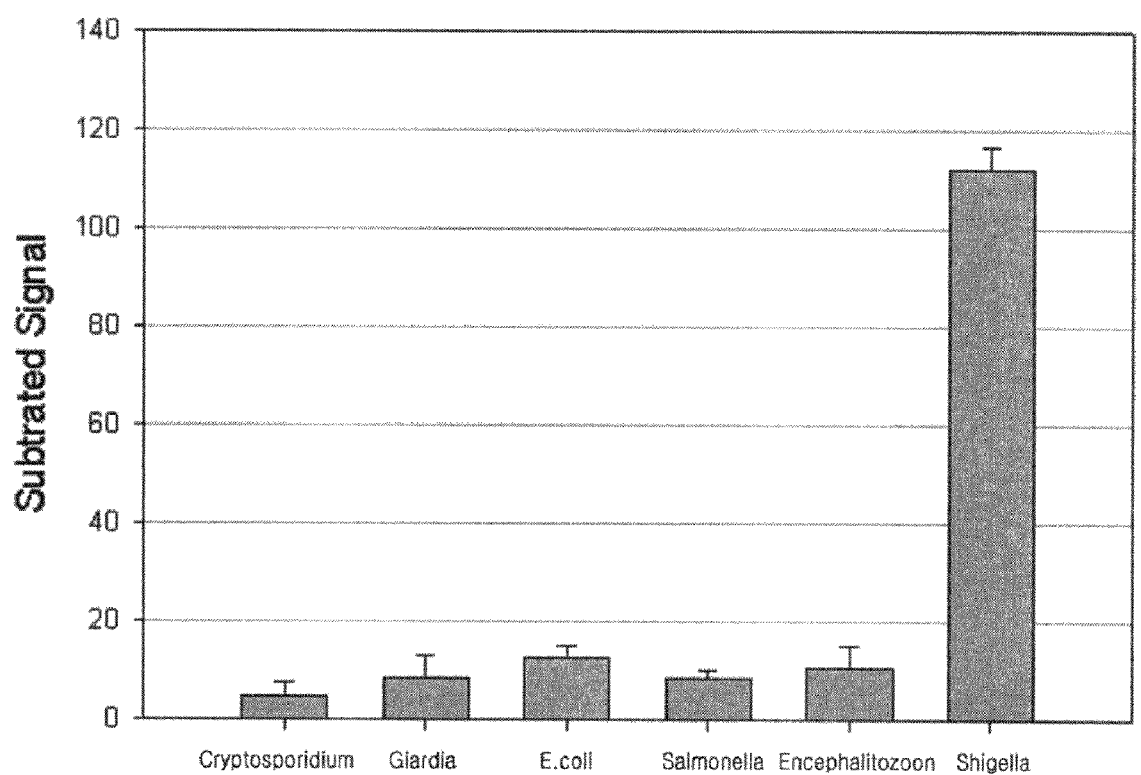
Figure 19:
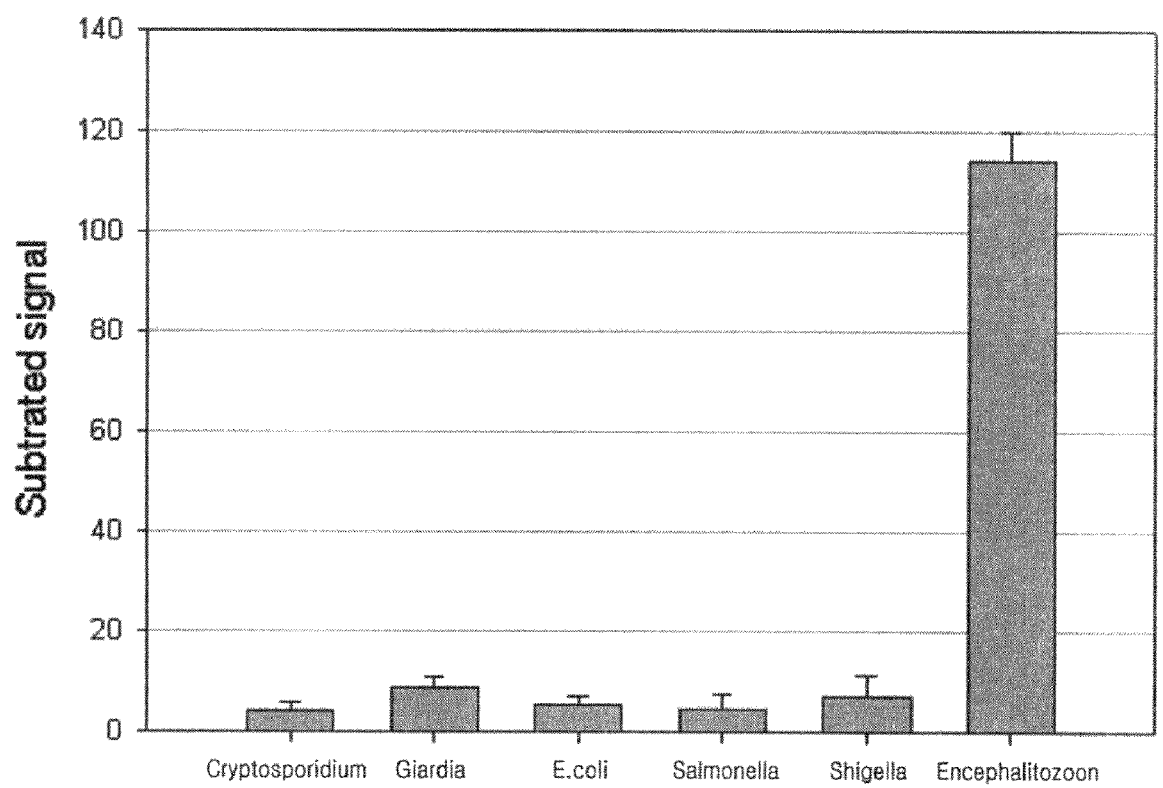

According to the aforementioned method, the polydiacetylene liposome sensor chip which was treated with diamine at the optimal concentration of 1 mM was exposed to UV light for about 5 minutes, and *C. parvum* (from $10^2$ unit/ml to $10^7$ unit/ml), *Giardia lamblia, E. coli* O-157, *Salmonella typhimurium, Shigella flexneri, Encephalitozoon intestinalis* (from $10^2$ unit/ml to $10^6$ unit/ml) were applied thereto at 37° C. Then, a fluorescent signals were observed and estimated by using an optical microscope. FIGS. 7 and 8 were obtained from the above experiment: FIG. 7 is a graph showing changes in detected signals upon *C. parvum* concentration; and FIG. 8 is a graph showing the exponential relation between the detected signal value and *C. parvum* concentration. FIG. 9 is a graph showing changes in detected signals upon *Giardia lamblia* concentration as well as the exponential relation between the detected signal value and *Giardia lamblia* concentration. FIGS. 10 to 13 are graphs showing changes in detected signals upon concentration of each *E. coli* O-157, *Salmonella typhimurium, Shigella flexneri* and *Encephalitozoon intestinalis* in this order, as well as the exponential relations between the detected signal value and the concentration of each pathogen.

From the results of FIGS. 7 to 13 which showed that the signals were increased constantly along the increase in cell concentration, it was found out that the standard curve as a function of cell concentration showed a linear form and the possible detection range was from the minimum of $10^2$ unit/ml to the maximum of $10^7$ unit/ml.

FIGS. 14 to 19 represent the analysis of fluorescent signals obtained by using a sensor chip comprising immobilized antibodies to *C. parvum* (FIG. 14), *Giardia, lamblia* (FIG. 15), *E. coli* O-157 (FIG. 16); *Salmonella typhimurium* (FIG. 17), *Shigella flexneri* (FIG. 18), and *Encephalitozoon intestinalis* (FIG. 19), to which the above 6 kinds of pathogens ($10^6$ unit/ml) were applied simultaneously for reaction. From the results shown in FIGS. 14 to 19, it can be found that that fluorescent signals were shown only in the pathogens which corresponded to the antibodies immobilized onto the sensor chip. Thus, it was confirmed that the chip for biomaterial detection according to the present invention did not react with a material that was not a target material, but specifically reacted with a target biomaterial.

According to the present invention, it is possible to detect biomaterials at low concentration in efficient way, by reinforcing the interlinks between the polydiacetylene liposomes owing to the use of an interlinker such as diamine so that multiple layers of polydiacetylene liposomes in a sensor chip can be formed, thereby amplifying the fluorescence signal. The present invention is expected to be widely used in various applications such as biosensor chips for biomaterial detection.

What is claimed is:

1. A method for detecting a biomaterial, which comprises the steps of:
   (S1) immobilizing polydiacetylene liposomes onto a substrate;
   (S2) linking the polydiacetylene liposomes together and layering them on the substrate, wherein the polydiacetylene liposomes are interlinked together by an interlinker comprising one or more functional groups selected from the group consisting of sulfone, amine and carboxyl group;
   (S3) immobilizing a material which forms a complementary binding with a subject biomaterial to be detected onto the polydiacetylene liposomes;
   (S4) exposing the resulted polydiacetylene liposomes to UV light, giving them a blue color, so as to form a chip for biomaterial detection;
   (S5) applying the subject biomaterial to be detected to the chip for biomaterial detection for reaction; and
   (S6) measuring a fluorescent signal from the chip for biomaterial detection.

2. The method for detecting a biomaterial according to claim 1, wherein the polydiacetylene liposome is prepared from a mixture of PCDA (10,12-Pentacosadiynoic-acid) and DMPC (1,2-Dimyristoyl-sn-Glycero-3-phosphocholine).

3. The method for detecting a biomaterial according to claim 2, wherein PCDA comprises one or more functional groups selected from the group consisting of sulfone, amine and carboxyl group.

4. The method for detecting a biomaterial according to claim 2, wherein the mixing ratio of PCDA and DMPC is between 9:1 and 6:4.

5. The method for detecting a biomaterial according to claim 2, wherein the temperature at the time of mixing PCDA and DMPC is between 4° C. and 100° C.

6. The method for detecting a biomaterial according to claim 1, wherein the step (S1) uses a NHS(N-Hydroxysuccinimide)/EDC(1-ethyl-3-[3-dimethylamino-propyl]carbodiimide hydrochloride) reaction between the amine groups substituted on the substrate and the carboxyl groups of the polydiacetylene liposomes.

7. The method for detecting a biomaterial according to claim 6, wherein the NHS/EDC reaction in the step (S1) is conducted at a temperature in the range of 0-37° C.

8. The method for detecting a biomaterial according to claim 1, wherein the concentration of the interlinker is more than 0 mM and not more than 20 mM.

9. The method for detecting a biomaterial according to claim 1, wherein the antibody immobilization in the step (S3) uses a NHS/EDC reaction.

10. The method for detecting a biomaterial according to claim 1, wherein in the step (S4), the polydiacetylene liposomes are exposed to UV light for 10 seconds to 10 minutes.

11. The method for detecting a biomaterial according to claim 1, wherein in the step (S5), the application of biomaterials to the chip for biomaterial detection for reaction is conducted at a temperature in the range of 0-50° C.

12. The method for detecting a biomaterial according to claim 1, wherein the subject biomaterial to be detected is selected from the group consisting of pathogens, DNA, RNA, PNA (Peptide Nucleic Acids), oligonucleotides, peptides, protein, biological membranes, polysaccharides, antigens, antibodies, and cells.

13. The method for detecting a biomaterial according to claim 12, wherein the pathogens are at least one selected from the group consisting of *Cryptosporidium parvum, Giardia lamblia, E. coli* O-157, *Salmonella typhimurium, Shigella flexneri*, and *Encephalitozoon intestinalis*.

14. A method for fabricating a chip for biomaterial detection, which comprises the steps of:
 (S1) immobilizing polydiacetylene liposomes onto a substrate;
 (S2) linking the polydiacetylene liposomes together and layering them on the substrate, wherein the polydiacetylene liposomes are interlinked together by using an interlinker comprising one or more functional groups selected from the group consisting of sulfone, amine and carboxyl group;
 (S3) immobilizing a material which forms a complementary binding with a subject biomaterial to be detected onto the polydiacetylene liposomes; and
 (S4) exposing the polydiacetylene liposomes to UV light.

15. The method for fabricating a chip for biomaterial detection according to claim 14, wherein the polydiacetylene liposome is prepared from a mixture of PCDA and DMP.

16. The method for fabricating a chip for biomaterial detection according to claim 15, wherein PCDA comprises one or more functional groups selected from the group consisting of sulfone, amine and carboxyl group.

17. The method for fabricating a chip for biomaterial detection according to claim 14, wherein the subject biomaterial to be detected is selected from the group consisting of pathogens, DNA, RNA, PNA (Peptide Nucleic Acids), oligonucleotides, peptides, proteins, biological membranes, polysaccharides, antigens, antibodies, and cells.

18. The method for fabricating a chip for biomaterial detection according to claim 17, wherein the pathogens are at least one selected from the group consisting of *Cryptosporidium parvum, Giardia lamblia, E. coli* O-157, *Salmonella typhimurium, Shigella flexneri*, and *Encephalitozoon intestinalis*.

19. A chip for biomaterial detection, characterized by comprising multilayered polydiacetylene liposomes immobilized on a substrate, wherein the polydiacetylene liposomes have immobilized materials thereon which form a complementary binding with a subject biomaterial to be detected, and develop a blue color by UV light irradiation, and wherein the polydiacetylene liposomes are interlinked together by an interlinker, wherein the interlinker comprises one or more functional groups selected from the group consisting of sulfone, amine and carboxyl group.

20. The chip for biomaterial detection according to claim 19, wherein the polydiacetylene liposome is prepared from a mixture of 10,12-pentacosadiynoic acid (PCDA) and 1,2-dimyristoyl-sn-glycero-3-phosphocholine (DMP).

21. The chip for biomaterial detection according to claim 20, wherein PCDA comprises one or more functional groups selected from the group consisting of sulfone, amine and carboxyl group.

22. The chip for biomaterial detection according to claim 19, wherein the subject biomaterial to be detected is selected from the group consisting of pathogens, DNA, RNA, PNA (Peptide Nucleic Acids), oligonucleotides, peptides, proteins, biological membranes, polysaccharides, antigens, antibodies, and cells.

23. The chip for biomaterial detection according to claim 22, wherein the pathogens are at least one selected from the group consisting of *Cryptosporidium parvum, Giardia lamblia, E. coli* O-157, *Salmonella typhimurium, Shigella flexneri*, and *Encephalitozoon intestinalis*.

24. The chip for biomaterial detection according to claim 19, wherein the polydiacetylene liposomes are directly linked to one another by the interlinker.

25. The chip for biomaterial detection according to claim 19, wherein the interlinker binds with a functional group of the polydiacetylene liposomes.

26. The chip for biomaterial detection according to claim 25, wherein the interlinker comprises a functional group that is the same as the functional group of the polydiacetylene liposome.

* * * * *

UNITED STATES PATENT AND TRADEMARK OFFICE
CERTIFICATE OF CORRECTION

PATENT NO.         : 7,932,046 B2                                    Page 1 of 1
APPLICATION NO.    : 12/317954
DATED              : April 26, 2011
INVENTOR(S)        : Sang Jun Sim et al.

It is certified that error appears in the above-identified patent and that said Letters Patent is hereby corrected as shown below:

Col. 2, Line 29
  Delete "calorimetric"
  Insert --colorimetric--

Col. 8, Line 21
  Delete "," after Giardia

Signed and Sealed this
Nineteenth Day of February, 2013

Teresa Stanek Rea
*Acting Director of the United States Patent and Trademark Office*